United States Patent [19]

Lawson

[11] 4,306,069
[45] Dec. 15, 1981

[54] ENCAINIDE N-OXIDE

[75] Inventor: John E. Lawson, Evansville, Ind.

[73] Assignee: Mead Johnson & Company, Evansville, Ind.

[21] Appl. No.: 160,900

[22] Filed: Jun. 19, 1980

[51] Int. Cl.$^3$ ............................................. C07D 211/94
[52] U.S. Cl. ...................................... 546/234; 424/267
[58] Field of Search ......................................... 546/234

[56] References Cited

U.S. PATENT DOCUMENTS 3,931,195  1/1976  Dykstra et al. ...................... 546/234

OTHER PUBLICATIONS

S. J. Dykstra et al., J. Med. Chem., vol. 16 (1973), pp. 1015–1020.
J. E. Byrne et al., J. Pharmacology and Experimental Therapeutics, vol. 200 (1977), pp. 147–154.

Primary Examiner—Norma S. Milestone
Attorney, Agent, or Firm—Robert H. Uloth; Robert E. Carnahan

[57] ABSTRACT

4-Methoxy-N-[2-[2-(1-methyl-2-piperidyl)ethyl]-phenyl]-benzamide N-oxide is an antiarrhythmic agent having reduced toxicity and increased water solubility relative to the corresponding tertiary amine.

1 Claim, No Drawings

ENCAINIDE N-OXIDE

FIELD OF THE INVENTION

4-Methoxy-N-[2-[2-(1-methyl-2-piperidyl)ethyl]-phenyl]-benzamide N-oxide is a heterocyclic carbon compound of the piperidine series having an additional ring and having nitrogen attached indirectly to the piperidine ring by non-ionic bonding (Class 546, Subclass 229), an N-methylpiperidine N-oxide derivative.

DESCRIPTION OF THE PRIOR ART

Encainide is an antiarrhythmic compound which is also referred to in the literature as MJ 9067 (USAN And The USP Dictionary of Drug Names 1980, page 122, United States Pharmacopeial Convention, Inc., 12601 Twinbrook Parkway, Rockville, MD 20852, Library of Congress Catalog Card No. 72-88571). Encainide has the following structural formula.

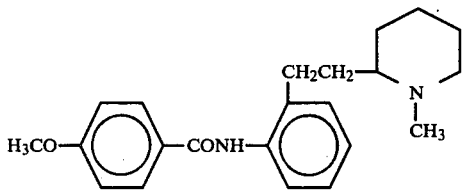

The following publications describe the chemical synthesis of encainide and the antiarrhythmic properties thereof in animals.

Dykstra, S. J., et al., J. Med. Chem., 16, 1015–1020 (1973).

Stanley J. Dykstra and Joseph L. Minielli, U.S. Pat. No. 3,931,195 patented Jan. 6, 1976.

Byrne, J. E., et al., J. Pharmacology and Experimental Therapeutics, 200, 147–154 (1977).

SUMMARY OF THE INVENTION

The present invention is concerned with encainide N-oxide which has the following structural formula.

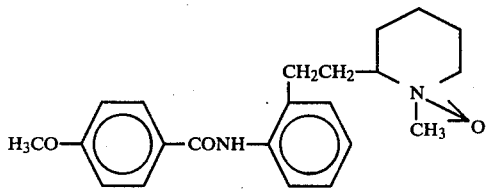

The present substance is an improved antiarrhythmic agent. In ouabain induced ventricular tachycardia in the dog (Byrne, et al., loc cit.), it is comparable to quinidine in activity, but somewhat less active than encainide. It is thus an antiarrhythmic agent of substantial potency and it offers the advantages over encainide of increased water solubility and reduced toxicity.

DETAILED DESCRIPTION OF THE INVENTION

Encainide has a rather low water solubility and is difficult to form into pharmaceutical tablets. The hydrochloride salt thereof has a higher water solubility relative to the base, presents no formulation difficulties, but possesses a bitter taste. The present substance represents an improvement over encainide and its hydrochloride salt in that it is highly water soluble and has substantially reduced toxicity. A comparison of the properties of encainide and encainide N-oxide is given in the following table.

| Property | Encainide | Encainide N-Oxide |
|---|---|---|
| Water solubility | 46.3 mg/ml. (hydrochloride salt, 205 mg/ml) | 833 mg/ml. |
| Toxicity | | |
| $ALD_{50}$[1] | 50–100 mg/kg | 500–1000 mg/kg |
| $ATD_{50}$[1] | 5–10 mg/kg | 62.5–125 mg/kg |
| Dog I.V.[2] | no effect @ 1 mg/kg lethal @ 10 mg/kg | no effect at 1 mg/kg and |
| Antiarrhythmic Activity | | |
| Dog, [3] I.V. | 2.43 mg/kg (av. 8 dogs) | 8.25 mg/kg (av. 2 dogs) |
| Mouse, [4] I.P. | $ED_{50}$ 7.1–15 mg/kg | inactive at 31.3 mg/kg |

[1] Various oral doses of from 5 mg/kg to 2000 mg/kg are given to 2 mice each; $ALD_{50}$ is the approximate lethal dose for half the animals; $ATD_{50}$ is the approximate lowest dose where signs of physiologic or neurologic deficit appear.
[2] Anesthesized dog treated first with a 1 mg/kg dose and then with a 10 mg/kg dose; effects on blood pressure, respiration, and paw temperature are observed.
[3] Anesthetized open chest dog, ouabain induced (Byrne, J.E., et al. loc. cit.).
[4] Ventricular arrhythmia produced in mice by chloroform inhalation, 10 animals per dose (Lawson, J. W., J. Pharmacol. Exp. Therap. 160, 22 (1968)).

DESCRIPTION OF SPECIFIC EMBODIMENTS

Encainide N-oxide may be prepared by any of a number of known methods which are general for the preparation of N-oxides by the oxidation of tertiary amines. The following procedure is representative.

PROCEDURE.—A solution of 10.58 g. (0.03 mole) of encainide in 79.5 ml. of methanol and 26.5 ml. (0.3 mole) of 30% hydrogen peroxide was allowed to stand at room temperature for three days. Excess hydrogen peroxide was then destroyed by adding the reaction solution in dropwise fashion to a stirred suspension of platinum black prepared by hydrogenating 300 mg. of platinum oxide in 100 ml. of 50% aqueous ethanol. The platinum was then removed by filtration, and the filtrate evaporated in vacuo to yield 11.84 g. of a light brown glass-like solid. The crude product was chromatographed on a 4.5 by 50 cm. column of alumina (Fisher A-540). Development with acetonitrile promptly removed 0.17 g. of unreacted encainide, and subsequent development with methanol provided the encainide N-oxide. The methanol eluate after evaporation of the solvent in vacuo, yielded 8.42 g., as a brittle white foam-like solid m.p. about 72° C. the composition of which corresponded to a monohydrate.

Anal. Calcd. for $C_{22}H_{28}N_2O_3 \cdot H_2O$: C, 68.37; H, 7.82; N, 7.25. Found: C, 68.32; H, 8.19; N, 7.17.

NMR: DMSO-$d_6$: 1.52 (8, m); 2.70 (5, m); 2.81, 2.82 (3, 2s); 3.84 (3, s); 7.20 (6, m); 8.15 (2, m); 10.72, 11.20 (1, bs).

IR: 770, 850, 1255, 1500, 1530, 1600, 1650, 2950, and 3270 cm$^{-1}$.

The nuclear magnetic resonance (NMR) values refer to chemical shifts (δ) expressed as parts per million (ppm) versus tetramethylsilane as reference standard. The relative area reported for the various shifts corresponds to the number of hydrogen atoms in the individual substituent and the nature of the shift as to multiplicity is reported as broad singlet (bs), singlet (s), or multiplet (m). The format is NMR (solvent): δ (relative area, multiplicity). The infrared (IR) was measured on a dispersion of the solid material in crystalline potassium bromide. The wave numbers of significant absorption maxima are listed.

The foregoing monohydrate when exposed to the room atmosphere at 26° C. for 24 hrs. until no further weight gain was apparent had a melting point of approximately 58° C. and was a glass-like solid corresponding in composition to the sesquihydrate.

Anal. Calcd. for $C_{22}H_{28}N_2O_3 \cdot 1.5H_2O$: C, 66.82; H, 7.91; N, 7.09; $H_2O$, 6.83. Found: C, 67.00; H, 7.71; N, 6.96; $H_2O$, 6.82.

A sample of the monohydrate prepared as described above was dried at 78° C. in a high vacuum (0.05 mmHg) for 24 hrs. over $P_2O_5$ as a dessicant. Constant weight was achieved within 4 hrs. The composition of the product after drying in this fashion corresponded to the ⅓ hydrate.

Anal. Calcd. for $C_{22}H_{28}N_2O_3 \cdot \tfrac{1}{3}H_2O$: C, 70.58; H, 7.72; N, 7.49; $H_2O$, 1.59. Found: C, 70.62; H, 7.62; N, 7.37; $H_2O$, 1.41.

Encainide N-oxide exists in four diastereoisomeric forms as a result of the presence of a second asymmetric center involving the piperidine nitrogen atom. This is reflected in the pair of singlets appearing at 2.81 ppm and 2.82 ppm in the foregoing nuclear magnetic resonance spectrum, and in the broadened singlets at 10.72 ppm and 11.20 ppm. The two racemates, the individual optical isomers, and mixtures thereof are considered part of the present invention.

What is claimed is:

1. 4-Methoxy-N-[2-[2-(1-methyl-2-piperidyl)ethyl]-phenyl]-benzamide N-oxide.

* * * * *